(12) United States Patent
Takagi et al.

(10) Patent No.: US 7,629,159 B2
(45) Date of Patent: Dec. 8, 2009

(54) NOCARDIOIDES FERM BP-10405 CAPABLE OF DEGRADING ORGANOCHLORINE PESTICIDE PCNB

(75) Inventors: Kazuhiro Takagi, No. 101, 11-916, Namiki 4-chome, Tsukuba-shi, Ibaraki 305-0044 (JP); Naoki Harada, Ibaraki (JP); Yuuichi Yoshioka, Kochi (JP)

(73) Assignees: National Institute for Agro-Environmental Sciences Independent Administration Institute, Ibaraki (JP); Kazuhiro Takagi, Ibaraki (JP); Kowa Co. Ltd., Aichi (JP)

( * ) Notice: Subject to any disclaimer, the term of this patent is extended or adjusted under 35 U.S.C. 154(b) by 311 days.

(21) Appl. No.: 11/335,686

(22) Filed: Jan. 20, 2006

(65) Prior Publication Data

US 2006/0166346 A1    Jul. 27, 2006

(30) Foreign Application Priority Data

| Jan. 26, 2005 | (JP) | ............................. 2005-018901 |
| Jun. 9, 2005 | (JP) | ............................. 2005-169369 |
| Jun. 29, 2005 | (JP) | ............................. 2005-189986 |

(51) Int. Cl.
*C12N 1/20* (2006.01)
*C12N 11/14* (2006.01)
*C12N 11/02* (2006.01)
*C12N 11/04* (2006.01)
*A62D 3/02* (2007.01)

(52) U.S. Cl. .................... 435/252.1; 435/176; 435/177; 435/182; 435/262.5; 435/822; 435/830

(58) Field of Classification Search ........................ None
See application file for complete search history.

(56) References Cited

U.S. PATENT DOCUMENTS

| 6,451,580 B1 | 9/2002 | Takagi et al. |
| 6,498,028 B1 | 12/2002 | Takagi et al. |
| 6,569,333 B1 | 5/2003 | Takagi et al. |

FOREIGN PATENT DOCUMENTS

| JP | 10-225288 | | 8/1998 |
| JP | 11-318435 | | 11/1999 |
| JP | 2003-250529 | * | 9/2003 |
| JP | 2005-027536 | | 2/2005 |
| WO | WO-00/78923 A1 | | 12/2000 |

* cited by examiner

*Primary Examiner*—David M Naff
(74) *Attorney, Agent, or Firm*—Cermak Kenealy; Vaidya & Nakajima LLP; Tomoko Nakajima

(57) ABSTRACT

The present invention provides a stable complex microbial system, which simultaneously decomposes a plurality of organic contaminants even under a polluted environment with these contaminants and permits more effective decomposition of persistent organic contaminants such as PCNB and simazine. A support for holding a complexed enrichment of degrading bacteria, which contains a porous material provided as a support on which degrading bacteria A capable of degrading at least one organic contaminant and degrading bacteria B capable of degrading another organic contaminant are enriched, is produced. The degrading bacteria A may be a PCNB-degrading bacteria, particularly degrading bacteria containing degrading bacteria having part or all of the bacteriological characteristics of *Nocardioides* sp. PD653 and the degrading bacteria B may be degrading bacteria containing degrading bacteria having part or all of the bacteriological characteristics of β-Proteobacteria CDB21.

1 Claim, 9 Drawing Sheets

LANE 1: CDB21+CSB1+CD7w+PD653
LANE 2: PD3+CD7 SURFACE DAY 0
LANE 3: PD3+CD7 SURFACE DAY 28
LANE 4: PD3+CD7 INSIDE DAY 0
LANE 5: PD3+CD7 INSIDE DAY 28
LANE 6: PD3+2Mix SURFACE DAY 0
LANE 7: PD3+2Mix SURFACE DAY 28
LANE 8: PD3+2Mix INSIDE DAY 0
LANE 9: PD3+2Mix INSIDE DAY 28

SEQUENCE LISTING

<160> NUMBER OF SEQ ID NOS: 2

<210> SEQ ID NO 1
<211> LENGTH: 1487
<212> TYPE: DNA
<213> ORGANISM: Nocardioides sp. PD653

<400> SEQUENCE: 1
gacgaacgct ggcggcgtgc ttaacacatg caagtcgagc ggtaaggccc tttcgggggt    60

-continued

| | |
|---|---|
| acacgagcgg cgaacgggtg agtaacacgt gagtaatctg cccttcactt ggggataagc | 120 |
| accggaaacg gtgtctaata cccgatacga ccaaccctg catgggtgt tggtggaaag | 180 |
| ttttttcggt gggggatgtg ctcgcggcct atcagcttgt tggtgggta atggcctacc | 240 |
| aaggcttcga cgggtagccg gcctgagagg gtgaccggcc acactgggac tgagacacgg | 300 |
| cccagactcc tacggaggc agcagtgggg aatattggac aatgggcgga agcctgatcc | 360 |
| agcaacgccg cgtgagggat gacggccttc gggttgtaaa cctctttcag cggggacgaa | 420 |
| gcgccgatga tggtggtgac ggtacccgca gaagaagcac cggccaacta cgtgccagca | 480 |
| gccgcggtaa tacgtagggt gcgagcgttg tccggaatta ttgggcgtaa agggctcgta | 540 |
| ggcggtttgt cgcgtcggga gtgaaaacac cgggcttaac tcggtgcttg ctttcgatac | 600 |
| gggcagacta gaggtatgca ggggagaacg gaattcctgg tgtagcggtg aaatgcgcag | 660 |
| atatcaggag gaacaccggt ggcgaaggcg ttctctggg cattacctga cgctgaggag | 720 |
| cgaaagtgtg gggagcgaac aggattagat accctggtag tccacaccgt aaacgttggg | 780 |
| cgctaggtgt ggggcctatt ccatgggttc cgtgccgcag ctaacgcatt aagcgccccg | 840 |
| cctggggagt acgccgcaa ggctaaaact caaaggaatt gacggggcc cgcacaagcg | 900 |
| gcggagcatg cggattaatt cgatgcaacg cgaagaacct tacctgggtt tgacatatgc | 960 |
| cggaaagccc cagagatggg gcccctttta gtcggtatac aggtggtgca tggctgtcgt | 1020 |
| cagctcgtgt cgtgagatgt tgggttaagt cccgcaacga gcgcaaccct cgtcctatgt | 1080 |
| tgccagcatg ccttcgggtg atggggactc ataggagact gccggggtca actcggagga | 1140 |
| aggtggggat gacgtcaagt catcatgccc cttatgtcca gggcttcacg catgctacaa | 1200 |
| tggccggtac aaagggctgc gatgctgtaa ggcggagcga atcccaaaaa gccggtctca | 1260 |
| gttcggattg gggtctgcaa ctcgacccca tgaagtcgga gtcgctagta atcgcagatc | 1320 |
| agcaacgctg cggtgaatac gttcccgggc cttgtacaca ccgcccgtca cgtcacgaaa | 1380 |
| gtcggcaaca cccgaagccg gtggcctaac ccttgtggag ggagccgtcg aaggtgggc | 1440 |
| tggcgattgg gacgaagtcg taacaaggta gccgtaccgg aaggtgc | 1487 |

<210> SEQ ID NO 2
<211> LENGTH: 831
<212> TYPE: DNA
<213> ORGANISM: Arthrobacter sp. CD7w

<400> SEQUENCE: 2

| | |
|---|---|
| atattgcaca atgggcggaa gcctgatgca gcgacgccgc gtgagggatg acggccttcg | 60 |
| ggttgtaaac ctctttcagt agggaagaag cgtaagtgac ggtacctgca gaagaagcgc | 120 |
| cggctaacta cgtgccagca gccgcggtaa tacgtagggc gcaagcgtta ccggaatta | 180 |
| ttgggcgtaa agagctcgta ggcggtttgt cgcgtctgcc gtgaaagtcc ggggctcaac | 240 |
| tccgatctg cggtgggtac gggcagacta gagtgatgta ggggagactg gaattcctgg | 300 |
| tgtagcggtg aaatgcgcag atatcaggag gaacaccgat ggcgaaggca ggtctctggg | 360 |
| cattaactga cgctgaggag cgaaagcatg ggagcgaac aggattagat accctggtag | 420 |
| tccatgccgt aaacgttggg cactaggtgt ggggacatt ccacgttttc cgcgccgtag | 480 |
| ctaacgcatt aagtgccccg cctggggagt acggccgcaa ggctaaaact caaaggaatt | 540 |
| gacggggcc cgcacaagcg gcggagcatg cggattaatt cgatgcaacg cgaagaacct | 600 |
| taccaaggct tgacatgaac cggaaacgcc tggaaacagg tgccccactt gtggtcggtt | 660 |
| tacaggtggt gcatggttgt cgtcagctcg tgtcgtgaga tgttgggtta agtcccgcaa | 720 |

-continued

```
cgagcgcaac cctcgttcta tgttgccagc acgtgatggt ggggactcat aggagactgc    780
cggggtcaac tcggaggaag gtggggacga cgtcaaatca tcatgcccct t             831
```

NOCARDIOIDES FERM BP-10405 CAPABLE OF DEGRADING ORGANOCHLORINE PESTICIDE PCNB

BACKGROUND OF THE INVENTION

1. Field of the Invention

The present invention relates to a technique for decomposing organic contaminants contained in crop land soil, underground water, or the like. In particular, the present invention relates to a technique for decomposing contaminants from soil, underground water, or the like, which has been contaminated by a plurality of organic contaminants, or to a technique for decomposing a persistent organic contaminant, by utilizing soil bacteria.

2. Description of the Related Art

In recent years, a bio-remediation technique, which is able to decontaminate contaminated soil or the like and make it safe by means of the natural degrading abilities of microorganisms such as bacteria, has attracted attention as a technique for decomposing persistent organic contaminants or POPs in low concentration distributed widely in crop land soil, or the like. However, in the conventional bio-remediation technique, even though someone wants to utilize microorganisms such as bacteria for decontamination effectively, the discovery of degrading bacteria that decompose an organic contaminant effectively has been difficult. Alternatively, even if the degrading bacteria can be discovered, the bacteria have its own living environment and the density of the degrading bacteria can be low in its natural state, so a contaminant cannot be effectively removed from the environment. In particular, in consideration of the application of the bio-remediation technique to contaminated soil or the like, problems have risen such that the degrading bacteria die as a result of effects of the physical and chemical properties of contaminated soil or predation by protozoa in the contaminated soil. Therefore, even though there are increasing demands for an effective bio-remediation technique, in actuality, such a technique has not yet spread widely.

On the other hand, the inventors of the present invention have found that a porous material having a predetermined absorption constant or specific surface can be utilized as a degrading bacterial habitat for organic contaminants and have developed technique for enriching and isolating a specific degrading bacterial species (Japanese Patent No. 3030370: Patent Document 1, Japanese Patent No. 2904432: Patent Document 2, and WO 00/078923: Patent Document 3). Those technologies have allowed any kind of organic contaminant which has been used in an agricultural chemical or the like and remained in environments, for example in soil, to be decomposed and removed by thickly enriching and purifying degrading bacteria capable of decomposing the organic contaminant.

In many cases, two or more organic contaminants may cause environmental contamination such as soil and water contamination. However, there is no in situ technique developed for simultaneously decomposing those contaminants.

In addition, it is difficult to decompose organic contaminants, such as organochlorine pesticide PCNB (quintozene: pentachloronitrobenzene), which is hardly decomposed, and simazine (2-chloro-4,6-bis (ethylamino)-1,3,5-triazine), which has a long half-life and a low soil-adsorption coefficient. Therefore, novel technique for more effectively decomposing the organic contaminants has been demanded in the art.

SUMMARY OF THE INVENTION

The present invention, therefore, intends to obtain a complex microbial system having stability, even in an environment contaminated with plural organic contaminants, which is capable of simultaneously decomposing these contaminants.

In addition, the present invention intends to decompose a persistent organic contaminant, such as PCNB or simazine in particular, more effectively.

To achieve the objects, according to one aspect of the present invention, there is provided a support for holding a complexed enrichment of degrading bacteria, including: a porous material; degrading bacteria A capable of degrading at least one organic contaminant, the degrading bacteria A being enriched on the porous material; and degrading bacteria B capable of degrading another organic contaminant, the degrading bacteria B being enriched on the porous material.

A support for holding a complexed enrichment of degrading bacteria is obtained by enriching degrading bacteria A capable of decomposing at least one organic contaminant and degrading bacteria B capable of decomposing another organic contaminant on a porous material, so that two or more organic contaminant can be decomposed. Here, the "degrading bacteria A" and the "degrading bacteria B" refer to different degrading bacteria, respectively. Each of the degrading bacteria A capable of decomposing at least one organic contaminant and the degrading bacteria B capable of decomposing another organic contaminant may be a single degrading bacterium, or may be provided as a bacterial group consisting of a combination of one or more symbiotic bacteria. The support for holding a complexed enrichment of degrading bacteria is able to decompose an organic contaminant such as triazine chemicals or organochlorine pesticides by being mixed in contaminated soil or being passed through contaminated water.

In addition, the degrading bacteria A may be PCNB-degrading bacteria, while the degrading bacteria B may be simazine-degrading bacteria. In this case, a support for holding a complexed enrichment of degrading bacteria, in which the enrichment is of at least one of the PCNB- and simazine-degrading bacteria or at least both of them in a porous material, can be obtained, thereby allowing PCNB or simazine or both of them to be decomposed from a processing object.

Furthermore, the degrading bacteria A may be any of degrading bacteria including bacteria having part or whole of bacteriological characteristics of *Nocardioides* sp. PD653 (hereinafter, simply referred to as "PD653"). In addition, the degrading bacteria B may be any of degrading bacteria including bacteria having part or whole of bacteriological characteristics of β-Proteobacteria CDB21. Consequently, a support for holding a complexed enrichment of degrading bacteria can be provided as one having at least one of *Nocardioides* sp. PD653 and β-Proteobacteria CDB21 or at least both of them enriched in a porous material, thereby allowing PCNB or simazine or both of them to be decomposed from a processing object.

Here, the degrading bacteria A may be provided as a bacterial group obtained by combining with one or more symbiotic bacteria. Besides, the degrading bacteria B may be provided as a bacterial group obtained by combining with one or more symbiotic bacteria. In other words, each of the degrading bacteria A and B may be not only a single bacterium but also a bacterial group containing two or more different bacterial species. Furthermore, when the degrading bacteria A or B forms a complex microbial system (consortium) in combination with at least one symbiotic bacterium, it is not a simple combination of bacterial group but one having functions of complementing essential nutrient factors required for the decomposition or assimilation of an organic contaminant or for the growth of bacteria with each other, thereby allowing an increase in degradation ability to the organic contaminant.

For instance, the degrading bacteria A may be PCNB-degrading bacteria PD3 (hereinafter, abbreviated as "PD3") and the degrading bacteria B may be either of simazine-degrading bacteria CD7 (hereinafter, abbreviated as "CD7") or simazine-degrading bacteria 2Mix (hereinafter, abbreviated as "2Mix"). Here, the term "PD3" refers to a consortium containing *Nocardioides* sp. PD653, *Burkholderia cepacia* KTYY97 (hereinafter, abbreviated as "KTYY97"), and other bacterial species. In addition, the term "CD7" refers to a consortium containing β-Proteobacteria CDB21 (hereinafter, abbreviated as "CDB21"), *Bradyrhizobium japonicum* CSB1 (hereinafter, abbreviated as "CSB1"), and *Arthrobacter* sp. CD7w (hereinafter, abbreviated as "CD7w"). Here, the term "2Mix" refers to a consortium containing β-Proteobacteria CDB21 and *Bradyrhizobium japonicum* CSB1.

The porous material used in the present invention may be one having an adsorption constant several ten times or more and at the same time ten thousand times or less as large as the adsorption constant of the soil where the degrading bacteria live, or having a specific surface area of from 50 cm$^2$/g to 600 m$^2$/g (both inclusive). In other words, when the porous material has an adsorption constant several ten times or more and at the same time ten thousand times or less as large as the adsorption constant of the soil where the degrading bacteria live, or having a specific surface area of from 50 cm$^2$/g to 600 m$^2$/g (both inclusive), an assimilation material can be easily adsorbed in the form of which the degrading bacteria can be easily accessible and thus degrading bacteria can be stably enriched on the support.

In addition, the porous material used in the present invention can be configured such that a volume ratio of pores having sizes that allow the fixation of degrading bacteria to the whole of pores is 10% or more. When the porous material is one in which a volume ratio of pores having sizes that allow the fixation of degrading bacteria to the whole of pores is 10% or more, the degrading bacteria can be easily propagated. Besides, the degrading bacteria can be stably grown. For satisfying such conditions, the pores having sizes ranging from 2 μm to 50 μm, preferably from 5 μm to 20 μm are preferably of 10% or more in volume ratio.

The porous material may be a carbonized ligneous material. When the porous material is the carbonized ligneous material, it is a suitable environment for the settlement of the degrading bacteria, thereby allowing the bacteria to be stably propagated and grown.

In addition, the present invention provides a bacterial strain that effectively decomposes an organochlorine pesticide PCNB. The bacterial strain may be a member of the genus *Nocardioides*, for example, *Nocardioides* sp. PD653 having a 16S rRNA (16s ribosomal RNA) gene containing a base sequence described in SEQ ID No: 1, which has been deposited as the Accession No. FERMP-20557 to the International Patent Organism Depositary, National Institute of Advanced Industrial Science and Technology with the address of Tsukuba Central 6, 1-1-1Higashi, Tsukuba, Ibaraki, Japan, and a bacterium having part or all of the mycologica characteristics of *Nocardioides* sp. PD653. Those bacteria are able to decompose PCNB completely in an effective manner.

Furthermore, the present invention provides a bacterial strain that lives in a symbiotic relationship with β-Proteobacteria CDB21 (FERM P-19395; which has been transferred control as the Accession No. FERM BP-10403 to the International Patent Organism Depositary, National Institute of Advanced Industrial Science and technology, Japan, on Aug. 22, 2005) that effectively decomposes triazine chemicals, particularly simazine. In particular, the bacterial strain is one grouped in *Arthrobacter,* such as *Arthrobacter* sp. CD7w deposited as the Accession No. FERM P-20371 at the International Patent Organism Depositary, National Institute of Advanced Industrial Science and Technology, Japan, and which has been transferred control as the Accession No. FERM BP-10404 to the same place on Aug. 22, 2005, and the bacterial strain may be a bacterial strain having part or whole of bacteriological characteristics of *Arthrobacter* sp. CD7w. The bacterial strain, which contributes to an improvement in degradation ability to simazine, has a 16S rRNA gene that contains a base sequence described in SEQ ID No: 2. Any of these bacteria may act as a consortium by symbiotically living with simazine-degrading bacteria (e.g., β-Proteobacteria CDB21) or the like to increase its affinity to the porous material. Therefore, the enrichment of simazine-degrading bacterial group on the porous material can be enhanced, thereby allowing higher degradation ability for triazine chemicals, particularly simazine, compared with the case in which only β-Proteobacteria CDB21 is present.

According to another aspect of the present invention, there is provided a method of producing a support for holding a complexed enrichment of degrading bacteria, including the following two steps of: (1) inoculating both degrading bacteria A capable of degrading at least one organic contaminant and degrading bacteria B capable of degrading another organic contaminant upon a porous material layer composed of laminated porous materials; and (2) adding each of an inorganic salt medium A, which contains the one organic contaminant as a sole carbon and nitrogen source, and an inorganic salt medium B, which contains the other organic contaminant as a sole carbon and nitrogen source, to the porous material layer after adjusting the concentration of each organic contaminant in the corresponding inorganic salt medium in proportion to an enrichment rate of each of the degrading bacteria A and B in the porous material when the inorganic salt media are added to the porous material layer; in which the degrading bacteria A and the degrading bacteria B are enriched and held on the porous material.

The method is designed to include the steps of: inoculating both degrading bacteria A capable of decomposing one organic contaminant and degrading bacteria B capable of decomposing another organic contaminant upon a porous material layer composed of laminated porous materials; and, when an inorganic salt medium A, which contains the one organic contaminant as a sole carbon and nitrogen source, and an inorganic salt medium B, which contains the another organic contaminant as a sole carbon and nitrogen source, are added to the porous material layer, adding the inorganic salt media to the porous material after adjusting the concentration of each organic contaminant in the corresponding inorganic salt medium in proportion to the enrichment rate of the corresponding degrading bacteria A or B in the porous material. Therefore, the desired amounts of the degrading bacteria A and B can be held in the porous material even when the growth rates of the degrading bacteria A and B are different from each other.

More specifically, the method of producing a support for holding a complexed enrichment of degrading bacteria may be one in which the step of adding each of the inorganic salt media to the porous material layer after adjusting the concentration of each organic contaminant in the corresponding inorganic salt medium in proportion to an enrichment rate of each of the degrading bacteria A and B in the porous material further includes sub-steps of: adding one of the inorganic salt media A and B to the porous material layer at once; and adding the other of the inorganic salt media A and B to the porous material layer under reflux.

In the step of adding each of the inorganic media after adjusting the concentration of the organic contaminant in each of the inorganic salt media in proportion to an enrichment rate of each of the degrading bacteria A and B in the porous material, one of the inorganic media A and B is added to the porous material layer at once, and the other of the inorganic media A and B is added to the porous material layer under reflux. Therefore, for example, the inorganic salt medium A to be provided as an assimilation material for the degrading bacteria A having a lower growth rate is added to the porous material all at once at the beginning, and the inorganic salt medium B to be provided as an assimilation material for the degrading bacteria B having a higher growth rate is supplied through a reflux solution. Thus, the degrading bacteria having a lower growth rate can be sufficiently propagated and grown without the occupation of niche (the habitat of degrading bacteria) by the degrading bacteria having a higher growth rate alone. Therefore, a support for holding a complexed enrichment of degrading bacteria, in which the degrading bacteria A and B live together, can be obtained. Here, the term "growth rate" means the rate of growth or multiplication of a bacterial group in the porous material.

Furthermore, the degrading bacteria A may be PCNB-degrading bacteria and also the degrading bacteria B may be simazine-degrading bacteria. In this case, therefore, a support for holding a complexed enrichment of degrading bacteria, in which the desired amounts of the PCNB-degrading bacteria and the simazine-degrading bacteria are held in the porous material, can be obtained.

Furthermore, the method of manufacturing a support for holding a complexed enrichment of degrading bacteria may be one in which the degrading bacteria A are degrading bacteria containing a degrading bacterial strain having part or all of the bacteriological characteristics of *Nocardioides* sp. PD653 and the degrading bacteria B are degrading bacteria containing a degrading bacterial strain having part or all of the bacteriological characteristics of β-Proteobacteria CDB21. In this case, therefore, a support for holding a complexed enrichment of degrading bacteria, in which the required amounts of the bacterial strain having part or all of the bacteriological characteristics of *Nocardioides* sp. PD653 and the bacterial strain having part or all of the bacteriological characteristics of β-Proteobacteria CDB21 are held in the porous material, can be obtained.

Here, each of the degrading bacteria A and the degrading bacteria B may be a single degrading bacterium or may be combined with one or more symbiotic bacteria to form a bacterial group. When a consortium is formed by making a combination with one or more symbiotic bacteria, the consortium is not a simple combination of bacterial group but one having functions of complementing essential nutrient factors required for the decomposition or assimilation of an organic contaminant or for the growth of bacteria with each other. In this case, therefore, a support for holding a complexed enrichment of degrading bacteria having increased degradation ability to the organic contaminant can be obtained.

Concretely, for example, the PCNB-degrading bacteria may be PCNB-degrading bacteria PD3 consisting of *Nocardioides* sp. PD653 and symbiotic bacteria thereof, *Burkholderia cepacia* KTYY97, and other bacterial groups. In addition, the simazine-degrading bacteria may be: simazine-degrading bacteria CD7 which are bacterial group containing three species, β-Proteobacteria CDB21, symbiotic bacteria thereof (*Bradyrhizobium japonicum* CSB1), and *Arthrobacter* sp. CD7w; or simazine-degrading bacteria 2Mix in which the simazine-degrading bacteria contain β-Proteobacteria CDB21 and symbiotic bacteria thereof (*Bradyrhizobium japonicum* CSB1).

According to another aspect of the present invention, there is provided a method of decontaminating a polluted environment, including the step of using a support for holding a complexed enrichment of degrading bacteria including: a porous material; degrading bacteria A capable of degrading at least one organic contaminant, the degrading bacteria A being enriched on the porous material; and degrading bacteria B capable of degrading another organic contaminant, the degrading bacteria B being enriched on the porous material.

A support for holding a completed enrichment of degrading bacteria, in which bacteria A capable of degrading at least one organic contaminant and bacteria B capable of degrading other organic contaminant are enriched on a porous material, is used. Therefore, it becomes possible to decompose at least two organic contaminants, thereby decontaminating a polluted environment.

The method of decontaminating a polluted environment can be designed such that the degrading bacteria A for decomposing one organic contaminant is PCNB-degrading bacteria and the degrading bacteria B for decomposing the other organic contaminant are simazine-degrading bacteria, or the degrading bacteria A are *Nocardioides* sp. PD653 or bacteria having part or all of the bacteriological characteristics of *Nocardioides* sp. PD653 and the degrading bacteria B are β-Proteobacteria CDB21 or bacteria having part or all of the bacteriological characteristics of β-Proteobacteria CDB21.

Furthermore, the method of decontaminating a polluted environment can be designed such that the degrading bacteria A are provided as a bacterial group obtained by making a combination with one or more symbiotic bacteria and the degrading bacteria B are provided as a bacterial group obtained by making a combination with one or more symbiotic bacteria. In other words, each of the degrading bacteria A and B can be provided as not only a single bacterial species but also a bacterial group containing a plurality of bacterial species. Besides, the method of decontaminating a polluted environment can be designed such that a complex microbial system (consortium) formed by combining the degrading bacteria A or B with its symbiotic bacteria are not a simple combination of bacterial group but one having functions of complementing essential nutrient factors required for the decomposition or assimilation of an organic contaminant, or for the growth of bacteria with each other, thereby allowing an increase in degradation ability to the organic contaminant.

PCNB and simazine, which are organic contaminants, can be decomposed when the degrading bacteria A are PCNB-degrading bacteria and the degrading bacteria B are simazine-degrading bacteria. In addition, when the degrading bacteria A are *Nocardioides* sp. PD653, bacteria having part or all of the bacteriological characteristics of *Nocardioides* sp. PD653, or PCNB-degrading bacteria PD3, while the degrading bacteria B are β-Proteobacteria CDB21, bacteria having part or all of the bacteriological characteristics of β-Proteobacteria CDB21, or simazine-degrading bacteria CD7 or 2Mix, each of PCNB and simazine can be almost completely (90% or more) decomposed. Likewise, organochlorine contaminants such as pentachlorophenol (PCP) and hexachlorobenzene (HCB) and triazine organic contaminants such as atrazine (2-chloro-4-ethylamino-6-isopropylamino-1,3,5-triazine) can be also decomposed.

According to another aspect of the present invention, there is provided a method of decontaminating a polluted environment, including: passing processing-object water through the support for holding a complexed enrichment of degrading bacteria and degrading an organic contaminant in the processing-object water to decompose the organic contaminant from the processing-object water.

The support for holding a complexed enrichment of degrading bacteria is designed such that processing-object water containing organic contaminants can pass through the support. Therefore, the organic contaminant in the processing-object water can be decomposed and removed by the degrading bacteria enriched in the support for holding a complexed enrichment of degrading bacteria, thereby decontaminating the processing-object water. Therefore, the contaminated processing-object water can be decontaminated by carrying out only a simple process of passing the processing-object water through the support for holding a complexed enrichment of degrading bacteria.

According to another aspect of the present invention, there is provided a method of decontaminating a polluted environment, including mixing the support for holding a complexed enrichment of degrading bacteria in processing-object soil to decompose one or more organic contaminants from the processing-object soil.

The support for holding a complexed enrichment of degrading bacteria is mixed in processing-object soil, so that organic contaminants contained in the soil can be transferred by rain water or the like to the support for holding a complexed enrichment of degrading bacteria and then decomposed. Therefore, by carrying out a simple processing of mixing the support for holding a complexed enrichment of degrading bacteria in the soil contaminated with organic contaminants, the organic contaminants in the contaminated soil can be decomposed and removed to decontaminate the contaminated soil.

Furthermore, the present invention provides a device for decontaminating a support for holding a complexed enrichment of degrading bacteria. The device for decontaminating a polluted environment contains a support for holding a complexed enrichment of degrading bacteria, so that organic contaminants can be easily decomposed and removed, thereby decontaminating a polluted environment.

By using the support for holding a complexed enrichment of degrading bacteria of the present invention, a plurality of organic contaminants contained in the contaminated soil and underground water can be simultaneously decomposed and the degradation ability of the support can be sustained in a stable manner.

The bacteria of the present invention can contribute to the complete decomposition of persistent PCNB and simazine.

The method of manufacturing a support for holding a complexed enrichment of degrading bacteria of the present invention can simply produce a support for holding a complexed enrichment of degrading bacteria in which two or more degrading bacterial species capable of decomposing different organic contaminants are enriched and held in a porous material.

According to the method and device of decontaminating a polluted environment of the present invention, the polluted environment can be decontaminated by simply decomposing two or more organic contaminants without requiring a complicated processing process.

The above description of the present invention should not be construed restrictively; the objects, advantages, features, and uses of the present invention will become still more apparent from the following description given with reference to the accompanying drawings. Further, it should be understood that all appropriate modifications made without departing from the gist of the present invention are covered by the scope of the present invention.

DETAILED DESCRIPTION OF THE PREFERRED EMBODIMENT

Figure 1:
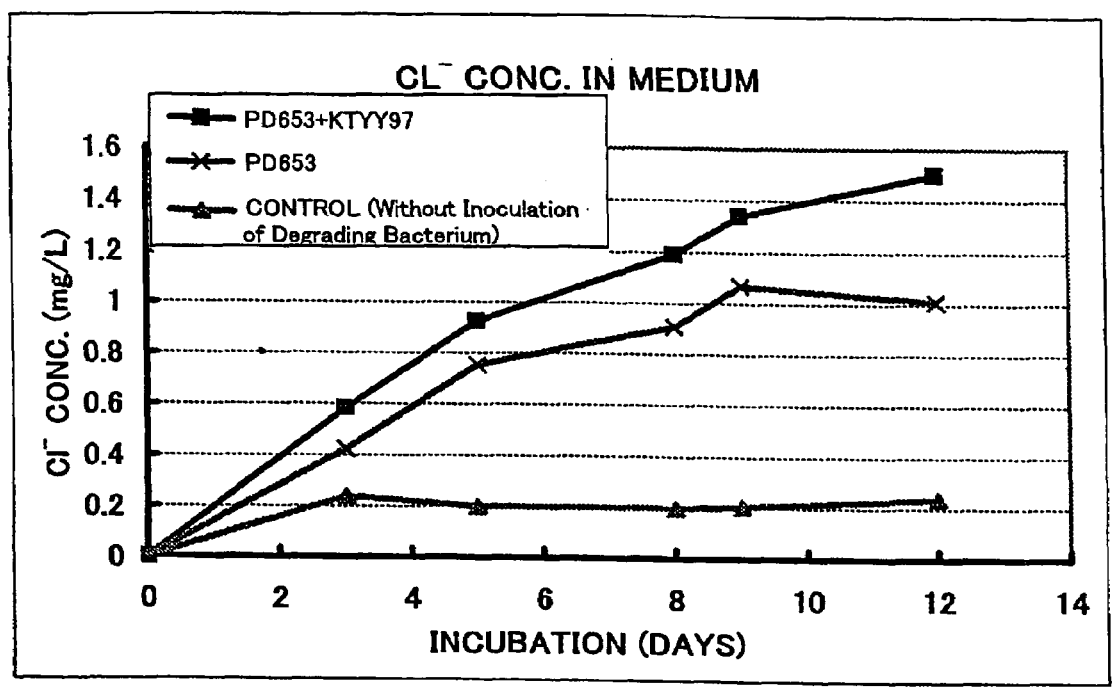
FIG. 1 is a graphical representation of the relationship between the number of incubation days for PCNB-degrading bacteria and the concentration of chloride ion.

Hereinafter, the support for holding a complexed enrichment of degrading bacteria and the bacteria of the present invention will be described in detail. The "support for holding a complexed enrichment of degrading bacteria" as used herein refers to enrichment of two or more degrading bacteria, which are capable of decomposing organic contaminants to be decomposed, at high density in a porous material.

Now, a support to be used in the support for holding a complexed enrichment of degrading bacteria and the degrading bacteria will be described below.

Support

The support for holding a complexed enrichment of degrading bacteria capable of decomposing organic contaminants may be a micro-habitat to be provided as a habitat of the degrading bacteria. The micro-habitat can be selected from porous materials each having many pores, a high adsorption coefficient, and a large effective surface area through which the degrading bacteria can be incorporated. That is, the specific surface is preferably from 50 $m^2/g$ to 600 $m^2/g$. In other words, the pore size is preferably from 2 μm to 50 μm, more preferably from 5 μm to 20 μm. Furthermore, it is preferable that such large-sized pores account for 10% or more of all of the pores in terms of volume percent. The porous material may be a carbonized ligneous material. For instance, a carbonized ligneous material A (5-mm to 10-mm chips of carbonized ligneous material obtained by subjecting broad leaved tree to general baking at 500° C., having a pH value of 8, a specific surface of 100 $m^2/g$, and the volumes of pores having diameters of 5 μm to 20 μm account for 10% or more of the total pore volume, as described in Japanese Patent No. 2904432) developed by the inventors of the present invention is an excellent micro-habitat. The carbonized ligneous material is preferably chipped into chips each having a size of about 2 mm to 15 mm. By the way, carbide such as activated carbon is not appropriate as a habitat of the degrading bacteria although such carbide can adsorb organic contaminants temporarily, the adsorption can be saturated immediately, thereby causing the need of replacing the carbide with new one. Therefore, the carbide is not sustainable to the stable use of extended period.

Degrading Bacteria

Degrading bacteria that decompose specific kinds of organic contaminants can be used. Those degrading bacteria used may be those having enhanced degradation ability obtained using a genetic recombinant technique or those newly created. However, regarding the safety evaluation of release of recombinant microorganisms to the environment, researches and discussions are still continuing and public acceptance has been difficult to obtain.

On the other hand, it is preferable to use degrading bacteria obtained by an improved soil reflux method which has been proposed by the inventors of the present invention because the degrading bacteria obtained by this method are one living in soil and thus, have a negligible problem in terms of safety. An improved soil reflux method forms an enrichment soil layer by mixing a porous material to be provided as a micro-habitat in soil where the degrading bacteria to be enriched live and then refluxes an inorganic salt medium contains only an organic contaminant to be decomposed by the degrading bacteria as a sole carbon and nitrogen source for the predetermined number of days. Next, the micro-habitat is taken out from the enrichment soil layer and then inoculated on another micro-habitat prepared to prepare an enrichment layer constructed only of the micro-habitat. An inorganic salt medium contains only an organic contaminant to be decomposed by the degrading bacteria as a sole carbon and nitrogen source is refluxed again through the enrichment layer to enrich the degrading bacteria of interest in a porous material. Alternatively, any degrading bacteria collected from soil by any other method may be used.

The isolation of degrading bacteria enriched in the porous material on the basis of the improved soil reflux method can be carried out by a dilution plate technique or the like. For instance, the porous material with enriched degrading bacteria is crushed and then suitably diluted with a phosphate buffer. Subsequently, the diluted solution is inoculated into an agar medium that contains a high concentration of an organic contaminant and then the whole is incubated. From a clear zone occurred in a plating medium, the bacterial cells are collected and then inoculated into a fresh agar medium, followed by incubation. In this way, a desired degrading bacterial colony is isolated.

A concrete example of the degrading bacteria include the following degrading bacteria.

PCNB-degrading bacteria PD3: The PCNB-degrading bacteria PD3 are a bacterial group consisting of a complex system of *Nocardioides* sp. PD653, *Burkholderia cepacia* KTYY97, and other bacteria.

Isolation of PD653, KTYY97, and other bacterial groups from the PCNB-degrading bacteria PD3 are carried out such that the bacteria are inoculated from the culture of PD3 to a R2A agar plate containing PCNB to isolate a purified colony and a part of the resulting colony is subjected to a tube culture to obtain a lineage. Finally, the resultant is incubated in a flask and then isolated therefrom.

*Nocardioides* sp. PD653 is a novel bacterial strain found by the inventors of the present invention and has been deposited as the Accession No. FERMP-20557 to the International Patent Organism Depositary, National Institute of Advanced Industrial Science and Technology with the address of Tsukuba Central 6, 1-1-1Higashi, Tsukuba, Ibaraki, Japan. *Nocardioides* sp. PD653 has degradation ability to PCNB and is grouped in the genus *Nocardioides* but not defined as a specific species.

PD653 has the following bacteriological characteristics. The incubation is carried out under the aerobic conditions on a R2A agar medium at 30° C. for 3 to 7 days. The morphological characteristics include a colony having no spore formulation, 1.0 mm in diameter at 3 days of the incubation, pale yellow, circular form, swelling like a half-lens form, smoothened entire fringe, opaque, and butter-like consistency. Variations in colony morphology due to mutation, and to incubation and physiological conditions are not recognized. The cell morphology is of bacillus having a size of about 0.7 to 0.8×1.0 to 1.2 μm without mobility and Gram-stained negative. Physiological characteristics are catalase: +, oxidase: −, acid/gas production (glucose): −/−, O/F test (glucose): −/−, and GC content: 70.8% (+: positive, −: negative).

On the basis of taxonomic characteristics with the phenotype of PD653 strain, the classification and identification thereof were carried out with reference to Bergey's Manual of Systematic Bacteriology, Vol. 1, N. R. Krieg, J. G. Holt (ed), Williams & Wilkins, Baltimore (1984). However, a short list of taxonomic groups having characteristic features analogous to those of PD653 could not be made.

Subsequently, as a result of molecular system analysis on the basis of a partial base sequence of 16S-rRNA gene of the PD653 strain of the present invention, when a homologous search to DNA data base (GeneBank/DDBJ/EMBL) is performed using FASTA and BLAST engines after determining continuous 1,487 bases in the base sequence of 16S-rRNA gene of PD653, the highest homology of 97.1% with *Nocardioides* sp. OS4 where the species has not been decided is shown. The results do not substantially conflict with the taxonomic characteristics of PD653 defined by its phenotype. Thus, PD653 is grouped in the genus *Nocardioides* sp. The above 1,487 bases are listed as SEQ ID NO: 1 in the sequence listing.

For investigating the degradation ability of PD653 to organic contaminants, PCNB having an initial concentration of 10 ppm was added to a medium containing 0.01% tripton and PD653 was then incubated at 30° C. in dark while shaking at 120 rpm, followed by determining the concentration of chlorine ions generated. As PCNB is decomposed, chlorine ions are generated, so the concentration of chlorine ions can be an indication of PCNB degradation. Incubation was carried out while shaking for 4 days under the conditions, whereby 4.5 ppm of chlorine ions are generated. Incubation was carried out while shaking for 16 days under the same conditions, whereby 13.3 ppm of chlorine ions are generated. In this way, PD653 had the degradation ability to PCNB alone. In addition, HCB having an initial concentration of 5 ppm is added instead of PCNB and then incubated 16 days while shaking under the same conditions, thereby generating 4.0 ppm of chlorine ions. From this, it is understood that PD653 had the degradation ability to HCB alone.

On the other hand, *Burkholderia cepacia* KTYY97 was deposited as FERM P-16809 and then transferred to the international deposit, followed by being deposited as FERM BP-6721 to the International Patent Organism Depositary, National Institute of Advanced Industrial Science and Technology, Japan. The details of the bacteria are described in Japanese Patent No. 2904432.

PCNB-degrading bacteria PD3 form a consortium by combining a plurality of bacteria such as PD653 and KTYY 97. An acetone solution of PCNB at an initial concentration of 6 ppm is added to each of a support for holding a complexed enrichment of degrading bacteria in which PD653 and KTYY97 are enriched in a porous material, and a support for holding a complexed enrichment of degrading bacteria in which only PD653 is enriched in a porous material is then incubated at 25° C. in the dark while shaking at 120 rpm. Variation in chloride ion concentration per day is shown in FIG. 1. PD653 has the PCNB degrading ability. However, as is evident from FIG. 1, when PD653 is combined with at least KTYY97, an increased amount of PCNB can be decomposed.

Examples of symbiotic bacteria capable of constituting a consortium together with PD653 or the like having PCNB-degradation ability include *Methylobacterium* sp. P4, *Microbacterium* sp. P42, and *Caulobacter* sp. P43 as well as KTYY97. The examples further include any bacteria other than those bacteria having abilities of assisting the growth of degrading bacteria and accelerating the decomposition of PCNB.

PD653 and KTYY97, which constitute the above PCNB-degrading bacteria PD3, are enriched and isolated using the improved soil reflux method. However, the present invention is not limited to them. PD653 is a bacterial strain grouped in the genus *Nocardioides,* which may be a bacterial strain having the ability of decomposing PCNB or a bacterial strain having part or all of the bacteriological characteristics of PD653. KTYY97 is a bacterial strain grouped in the genus *Burkholderia,* which may be a bacterial strain having part or all of the bacteriological characteristics of KTYY97.

Simazine-degrading bacteria CD7: Simazine-degrading bacteria (CD7) are a bacterial group, which consists of three kinds of strain, β-Proteobacteria CDB21, *Bradyrhizobium japonicum* CSB1, and *Arthrobacter* sp. CD7w.

Isolation of CDB21, CSB1, and CD7w from the simazine-degrading bacteria CD7 is carried out such that the bacteria are inoculated from the culture of CD7 to a bactotrypsin agar plate containing simazine to isolate a purified colony. CDB21, CSB1, and CD7w can be obtained as three colonies having different configurations.

β-Proteobacteria CDB21 are a novel bacterial strain discovered by the inventors of the present invention and is grouped in the genus β-Proteobacteria, but not in any species thereof known in the art. β-Proteobacteria CDB21 have been deposited as FERM P-19395 to the International Patent Organism Depositary, National Institute of Advanced Industrial Science and Technology, Japan, and have been transferred control as the Accession No. FERM BP-10403 to the same place on Aug. 22, 2005. Only CDB21 possesses simazine-degradation ability of the simazine-degrading bacteria CD7.

*Bradyrhizobium japonicum* CSB1 belongs to a category of *Bradyrhizobium japonicum* and has been deposited as FERM P-19394 to the International Patent Organism Depositary, National Institute of Advanced Industrial Science and Technology, Japan, and has been transferred control as the Accession No. FERM BP-10402 to the same place on Aug. 22, 2005.

*Arthrobacter* sp. CD7w is also a novel bacterial strain, which has been deposited as the Accession No. FERM P-20371 to the International Patent Organism Depositary, National Institute of Advanced Industrial Science and Technology, Japan, and which has been transferred control as the Accession No. FERM BP-10404 to the same place on Aug. 22, 2005.

CD7w has the following bacteriological characteristics. The incubation is carried out under the aerobic conditions on a NA medium at 30° C. for 2 to 3 days. The morphological characteristics include a colony having no spore formation, 1 to 3 mm in diameter at 2 days of the incubation, pale yellow, circular form, swelling like a half-lens form, smoothened entire fringe, opaque, and butter-like consistency. Variations in colony morphology due to mutation and to incubation and physiological conditions are not recognized. The cell morphology is of bacillus having a size of about 0.8×1.2 m with mobility and Gram-stained positive. Physiological characteristics are catalase: +, oxidase: −, O/F test: −, nitric acid reduction: −, pyrazinamidase: +, pyrrolidonyl allyl amidase: −, alkali phosphatase: −, β-glucuronidase: −, β-galactosidase: −, N-acetyl-β-glucosaminidase: −, esculin (glucosidase): +, urease: −, liquefaction of gelatin: +, fermentability of carbohydrate is glucose: −, ribose: −, xylose: −, mannitol: −, maltose: −, lactose: −, saccarose: +, and glycogen: − (+: positive, −: negative).

Classification and identification of CD7w on the basis of the taxonomic characteristic of CD7w's phenotype were performed, and the result indicated that the CD7w was genus *Arthrobacter* in reference to Bergey's Manual of Systematic Bacteriology, Vol. I, N. R. Krieg, J. G. Holt (ed.), Williams & Wilkins, Baltimore (1984), and Bergey's Manual of Determinative Bacteriology (9th ed.), J. G. Holt, N. R. Krieg, P. H. A, Sneath, J. T. Staley, S. T. Williams (ed.), Williams & Wilkins, Baltimore (1994).

As a result of molecular system analysis on the basis of the base sequence of 16S-rRNA gene with respect to CD7w, continuous 831 bases in the base sequence of 16S-rRNA gene of CD7w were determined. When a homologous search to DNA data base (GeneBank/DDBJ/EMBL) is carried out using FASTA and BLAST engines, the highest homology of 99.9% with *Arthrobacter* sp. Ellin 146 where the species has not been decided is shown. Subsequently, CD7w is grouped into *Arthrobacter* sp. The above 831 bases are listed as SEQ ID NO: 2 in the sequence listing.

Any of CDB21, CSB1, and CD7w is hardly grown alone in an inorganic salt medium containing simazine as a sole carbon and nitrogen source, so that any distinct colony cannot be formed. Those combinations allow a colony to emerge when at least CDB21 and CSB1 are combined. Therefore, the simazine-degrading bacteria CD7 are not a simple combination of bacteria but form a consortium having functions of complementing essential nutrient factors required for the decomposition or assimilation of simazine or for the growth of bacteria with each other.

When the existence of the simazine-degrading bacteria CD7 in the porous material is investigated, among them, CD7w is scarcely present on the surface of the porous material but highly enriched inside thereof. Therefore, in the consortium of CD7w, CDB21, and so on, CD7w has a function to improve affinity of CDB21 to porous material and enrich CDB21 in a high density therein, that is hardly achieved by only CDB21 or the like.

Bacterial symbionts capable of constituting consortia together with CDB21 and the like having the ability for degrading simazine include *Rhodococcus rhodochrous, Stenotrophomonas maltophilia, Nocardioides jensenii, Nocardioides fulvus, Nocardioides* simplex, and *Pseudomonas aeruginosa* as well as *Bradyrhizobium japonicum* such as CSB1 and *Arthrobacter* such as CD7w. Bacterial symbionts capable of constituting consortia together with CDB21 and the like having the ability for degrading simazine also include bacteria having an ability for support of degrading bacteria growth or enhancement of degrading simazine in addition to the bacteria described above.

CDB21, CSB1, and CD7w, which constitute the above simazine-degrading bacteria CD7, are those enriched and isolated using an improved soil reflux method but the present invention is not limited thereto. Alternatively, CDB21 is a bacterial strain grouped in β-Proteobacteria having simazine-degradation ability, which may be a bacterial strain having part or all of the bacteriological characteristics of CDB21. In addition, CSB1 is a bacterial strain grouped in *Bradyrhizobium japonicum*, which may be a bacterial strain having part or all of the bacteriological characteristics of CSB1. Furthermore, CD7w may be a bacterial strain grouped in *Arthrobacter* having ability to assist the degradation of simazine and the growth of a symbiotic bacterial strain or may be a bacterial strain having part or all of the bacteriological characteristics of CD7w.

Simazine-degrading bacteria 2Mix: Simazine-degrading bacteria 2Mix are a bacterial group consisting of a complex of two species, β-Proteobacteria CDB21 and *Bradyrhizobium japonicum* CSB1, and are simazine-degrading bacteria CD7 with a lack of CD7w. In other words, the simazine-degrading bacteria 2Mix have simazine-degrading ability in spite of lacking CD7w and exert its functions as the simazine-degrading bacteria.

Method of Manufacturing a Support for Holding a Complexed Enrichment of Degrading Bacteria:

Next, the method of manufacturing a support for holding a complexed enrichment of degrading bacteria of the present invention, where the porous material and the degrading bacteria described above are used, will be described. For instance, on a sintered glass filter 2 placed in a reflux device 1, a porous material 3 to be provided as a micro-habitat is filled and subjected to a sterilization process in advance. To the porous material 3, only an organic contaminant, which is provided as an assimilation material of degrading bacteria having a lower growth rate among the degrading bacteria to be enriched, is dissolved and added. Next, one degrading bacteria and another degrading bacteria to be enriched are inoculated to the porous material 3. After that, an inorganic salt medium 4 is refluxed for a suitable time period. Here, the inorganic salt medium contains only an organic contaminant to be provided as an assimilation material of degrading bacteria having a rapid growth rate among the degrading bacteria to be enriched as a sole carbon and nitrogen source. The reflux is carried out without drying the porous material 3 and without allowing the inorganic salt medium 4 to overflow from the porous material 3, thereby passing a constant amount of the inorganic salt medium 4 through the porous material 3. The reflux solution may preferably be replaced with new one about once per week. In addition, when the reflux solution is replaced, the organic contaminant to be provided as an assimilation material of the degrading bacteria having a lower growth rate is added to the porous material 3 in the same manner as one performed at the time of reflux. An objective support for holding a complexed enrichment of degrading bacteria can be obtained by repeating the addition and reflux of the organic contaminant. By the way, the method of manufacturing the support for holding a complexed enrichment of degrading bacteria is not limited to one using the device, and any device can be used as long as it can repeat the addition and reflux.

Method of Decontaminating Polluted Environment:

For decontaminating an environment pollued with an organic contaminant using a support for holding a complexed enrichment of degrading bacteria, the following usage can be given.

For the removal of an organic contaminant from contaminated soil, there is a usage in which the support for holding a complexed enrichment of degrading bacteria of the present invention is embedded in the contaminated soil and then mixed together. The organic contaminant in the soil may migrate (diffuse or transfer) together with rain water or the like, followed by being adsorbed into the support for holding a complexed enrichment of degrading bacteria and decomposed by the degrading bacteria. Likewise, furthermore, an organic contaminant which can be newly applied or the like is also adsorbed in the support for holding a complexed enrichment of degrading bacteria and decomposed, thereby preventing enrichment and diffusion of the organic contaminant in soil thereafter. According to this method, the contamination of an organic contaminant in soil into underground water can be prevented and underground water can be also prevented from contamination. As an application of this technique, an organic contaminant can be processed by mixing into: the surface layer or lower layer soil in which contaminants or the like can be present; the lower layer soil of a green surface of a golf course; the lower layer soil of an industrial waste processing facility; or the lower layer soil of a place for an organic waste solution.

In addition, if a carrier enrichment layer is formed such that the support for holding a complexed enrichment of degrading bacteria of the present invention is packed in a housing with air permeability, it can be provided as a simple bioreactor to serve as a device for decomposing an organic contaminant. The device may be placed in a part of water conduit such as a domestic drainage canal, an agricultural drainage canal in a paddy field zone, or a drainage cannel in a golf course, thereby decomposing an organic contaminant being dissolved and dispersed in water to decontaminate a polluted environment. In addition, in case of emergency, the support for holding a complexed enrichment of degrading bacteria of the present invention may be directly applied by dispersing on a contaminated area.

EXAMPLES

Hereinafter, the present invention will be described in further detail with respect to the following examples. However, the present invention is not limited to the examples.

Figure 2:
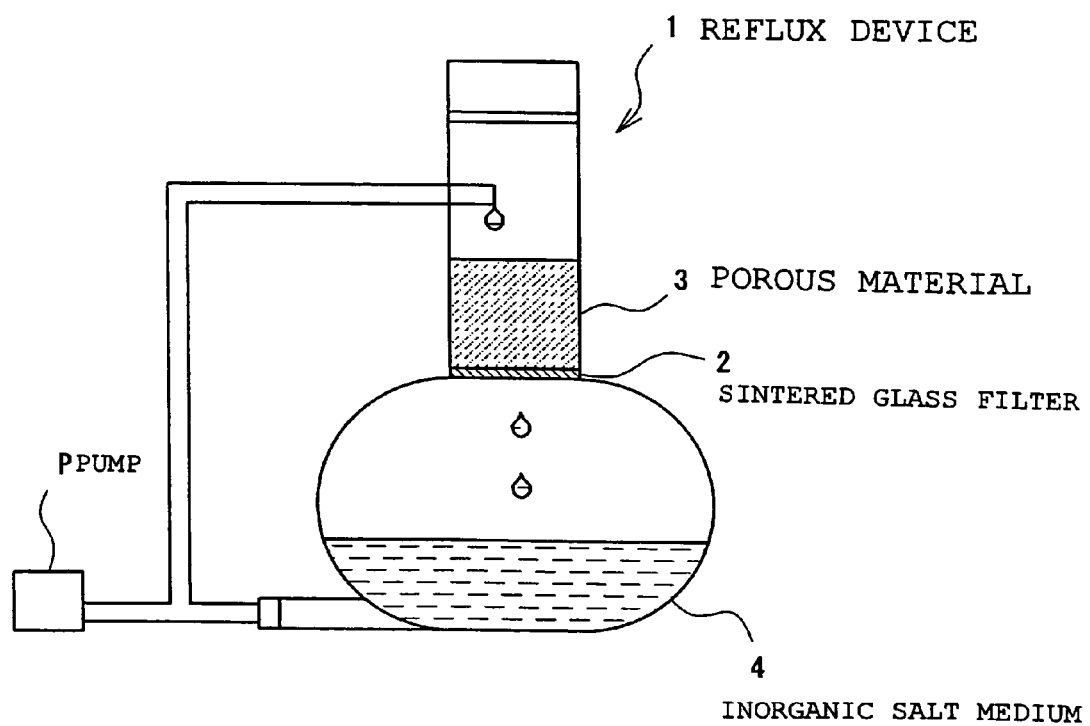
FIG. 2 is an external representation of a reflux device.

1. Method of Manufacturing a Support for Holding a Complexed Enrichment of Degrading Bacteria:

Support for holding a complex enrichment of degrading bacteria, on which PD3 and CD7 are held: A reflux device 1 shown in FIG. 2 was filled with about 7.5 g of a carbonized ligneous material A (5-mm to 10-mm chips of carbonized ligneous material obtained by subjecting broad leaved tree to general baking at 500° C., having a pH value of 8, a specific surface of 100 m$^2$/g, and the volumes of pores having diameters of 5 μm to 20 μm account for 10% or more of the total pore volume, as described in Japanese Patent No. 2904432) 3 to serve as a micro-habitat and then washed with ultrapure water, followed by subjecting to a sterilization process. The porous material 3 was added with 0.5 ml of a 3,000-ppm PCNB acetone solution and then inoculated with two colonies of each of PCNB-degrading bacteria PD3 and simazine-degrading bacteria CD7. Subsequently, 4,300 ml of a 5-ppm simazine inorganic salt medium (medium containing diammonium phosphate, dipotassium phosphate, monosodium phosphate, magnesium sulfate, and so on) was refluxed at 25° C. The reflux solution was replaced with new one once per week and at this time 0.5 ml of a 3,000-ppm PCNB acetone solution was newly added to the porous material 3. The reflux was carried out for three weeks. In this way, a support for holding a complexed enrichment of degrading bacteria of the present invention, in which the PCNB-degrading bacteria PD3 and the simazine-degrading bacteria CD7 were enriched in the carbonized ligneous material A 3, was obtained.

The total amount of PCNB to be provided as an assimilation material of the PCNB-degrading bacteria PD3, which was dissolved in acetone, was directly added to a porous material at first. On the other hand, simazine to be provided as an assimilation material of the simazine-degrading bacteria CD7 were added at a low concentration (5 ppm) to an inorganic salt medium, followed by refluxing. Therefore, the assimilation materials are added by different procedures, so that a support for holding a complexed enrichment of degrading bacteria, in which the required amounts of the PCNB-degrading bacteria PD3 and the simazine-degrading bacteria CD7 are retained in the carbonized ligneous material A can be obtained. However, if both PCNB and simazine are added at once to the porous material, the simazine-degrading bacteria CD7 having a higher growth rate occupies the porous material and most of the enrichment of the PCNB-degrading bacteria PD3 are not present. Simazine is dissolved in an inorganic salt medium and refluxed to control the rate of adsorption to the porous material, thereby lowering the enrichment rate of the simazine-degrading bacteria CD7.

Support for holding a complex enrichment of degrading bacteria, in which PD3 and 2Mix are held: The production of a support for holding a complexed enrichment of degrading bacteria was carried out such that a complex microbial system of the PCNB-degrading bacteria PD3 and the simazine-degrading bacteria 2Mix were constructed. A support for holding a complex enrichment of degrading bacteria, in which PD3 and 2Mix were held, was obtained by the same way as in the production of the support for holding a complex enrichment of degrading bacteria, in which PD3 and CD 7 were held, except that 2Mix was used instead of CD7.

Support for holding a complex enrichment of degrading bacteria, in which PD3, CD7, or 2Mix were held independently: A support for holding a complex enrichment of degrading bacteria, in which the PCNB-degrading bacteria PD3, the simazine-degrading bacteria CD7, or the simazine-degrading bacteria 2Mix were independently enriched (hereinafter, referred to as a "single fraction"), was produced. The production of a single fraction was also carried out by the same way as that of the support for holding a complex enrichment of degrading bacteria, PD3 or CD7. In this case, however, two colonies of the degrading bacterial culture to be enriched are inoculated to the porous material, so that only the assimilation material of the target degrading bacteria can be provided. In other words, a 3,000-ppm PCNB acetone solution was not added before the reflux. For the production of the PCNB-degrading bacteria PD3, only 300 ml of a 5-ppm PCNB inorganic salt medium was refluxed. On the other hand, for the production of the simazine-degrading bacteria CD7 or 2Mix, only 300 ml of a 5-ppm simazine inorganic salt medium was refluxed to enrich the degrading bacteria.

The resulting support for holding a complex enrichment of degrading bacteria was confirmed and evaluated as follows.

2. Confirmation of Enrichment Status of Degrading Bacteria into Porous Material [FIGS. 3 to 5]

Figure 3:
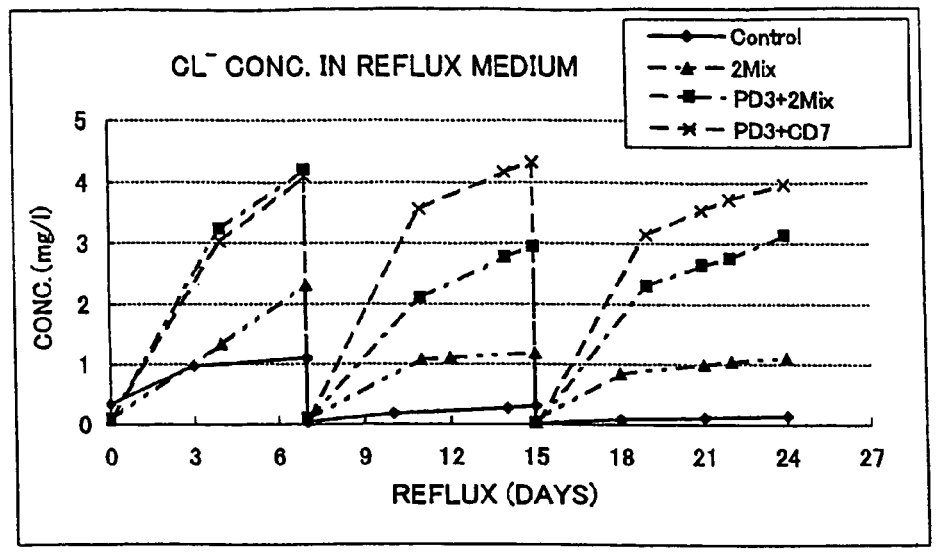
FIG. 3 is a graphical representation of the relationship between the number of reflux days and the concentration of chloride ion at the time of manufacturing a support for holding a complexed enrichment of degrading bacteria.
Figure 4:
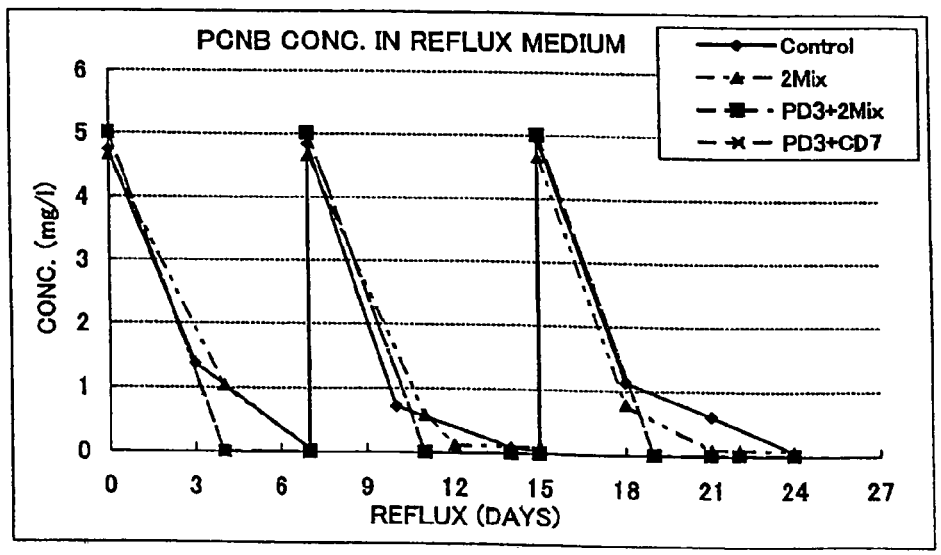
FIG. 4 is a graphical representation of the relationship between the number of reflux days and the concentration of PCNB at the time of manufacturing a support for holding a complexed enrichment of degrading bacteria.
Figure 5:
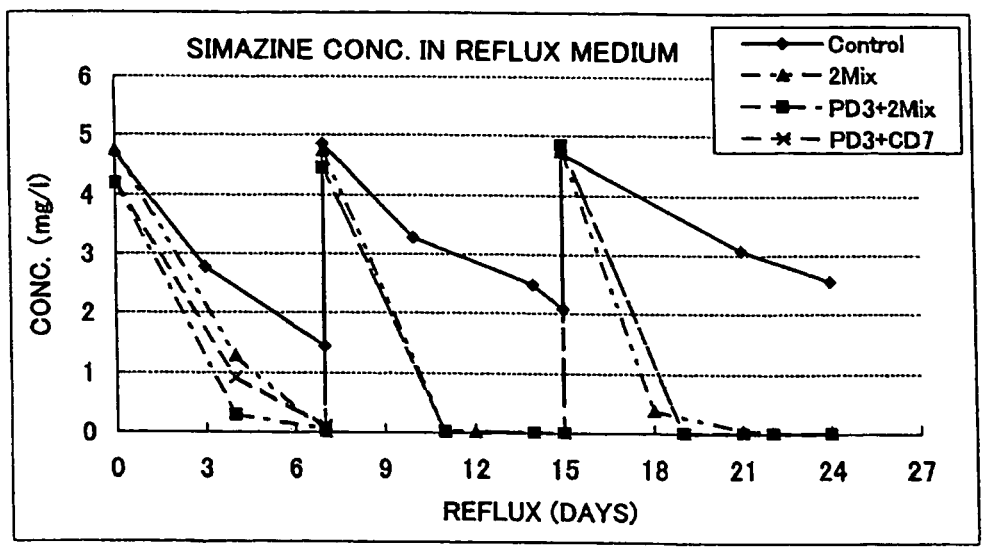
FIG. 5 is a graphical representation of the relationship between the number of reflux days and the concentration of simazine at the time of manufacturing a support for holding a complexed enrichment of degrading bacteria.

For confirming the enrichment status of degrading bacteria in the porous material, the measurement of chlorine ion concentration as a decomposition product of PCNB or simazine was carried out from the initiation to termination of reflux. The chlorine ion concentration with respect to the number of reflux days is shown in FIG. 3. On the other hand, the measurement of PCNB and simazine concentrations was also carried out. The disappearance status of PCNB is shown in FIG. 4 and the disappearance status of simazine is shown in FIG. 5, respectively. The chlorine ion concentration obtained when PCNB and simazine are completely decomposed was 3.9 ppm. Thus, as shown in FIGS. 4 and 5, it is found that PCNB and simazine can be almost completely decomposed by carrying out reflux for 2 to 3 weeks. The growth environment of bacteria and the acquisition, conjugate metabolism, and co-localization of niche of the bacteria in competition with other bacteria are problems inherent to the bacterial. It is found that the PCNB-degrading bacteria PD3, and the simazine-degrading bacteria CD7 and 2Mix can be enriched in sufficient amounts for decomposing PCNB and simazine. This can be proved from the disappearance status of PCNB or simazine.

3. Evaluation on the Number of Bacterial Cells of the Degrading Bacteria Enriched in Porous Material [FIGS. 6 and 7]

The number of bacterial cells of the degrading bacteria enriched in a support for holding a complexed enrichment of degrading bacteria was also evaluated. Evaluation on the number of bacterial cells of the degrading bacteria enriched in a support for holding a complexed enrichment of degrading bacteria was carried out such that, after the reflux operation, 2 g of the porous material was taken off, added with 18 ml of a phosphate buffer, and then subjected to ultrasonication for 2 minutes. As a result, the degrading bacteria attached on the surface of the carbonized ligneous material A were removed from the carbonized ligneous material A and then the carbonized ligneous material A was taken from the buffer to obtain a "$10^1$-fold dilute solution". On the other hand, the removed carbonized ligneous material A was ground up into a pulverized product. Then, 1.0 g of the pulverized product was added with 9 ml of a phosphate buffer and the whole was shaken for 30 minutes, followed by ultrasonication for 1 minute to obtain a "$10^1$-fold dilute solution". Each of the $10^1$-fold dilute solutions was further serially diluted in an appropriate manner to obtain dilute solutions with five different dilution stages. A 1-ml aliquot was taken from each of the dilute solutions and then added to each of ten tubes in total where five tubes each contained 5 ppm of simazine inorganic salt medium and the other five tubes each contained 5 ppm of PCNB inorganic salt medium. Subsequently, those samples were incubated at 25° C. for 2 weeks and then the chlorine ion concentration of each sample was determined. Any sample having a chlorine ion concentration of 0.5 ppm or more was defined as "+". Besides, for each of the samples, the number of degrading bacterial cells on the surface of, or inside, the carbonized ligneous material A was determined using a MPN method.

Figure 6:
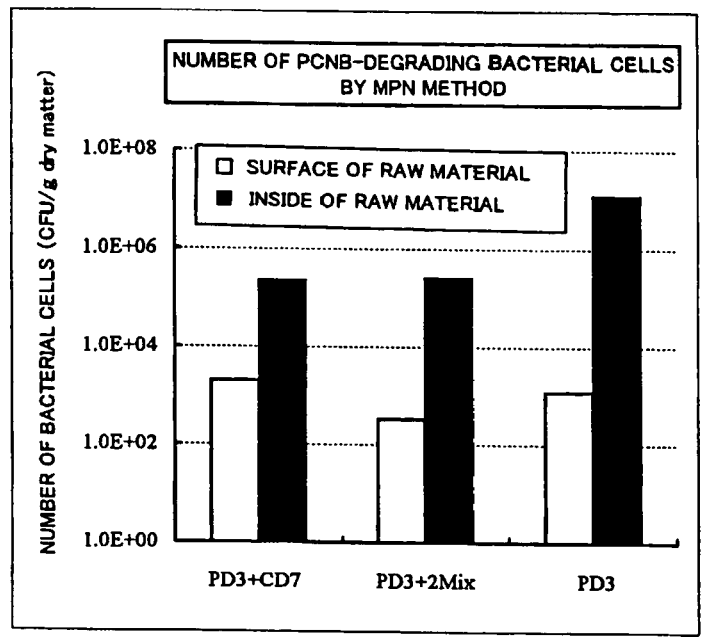
FIG. 6 is a graphical representation of the number of bacterial cells of the PCNB-degrading bacteria enriched on the support for holding a complexed enrichment of degrading bacteria.
Figure 7:
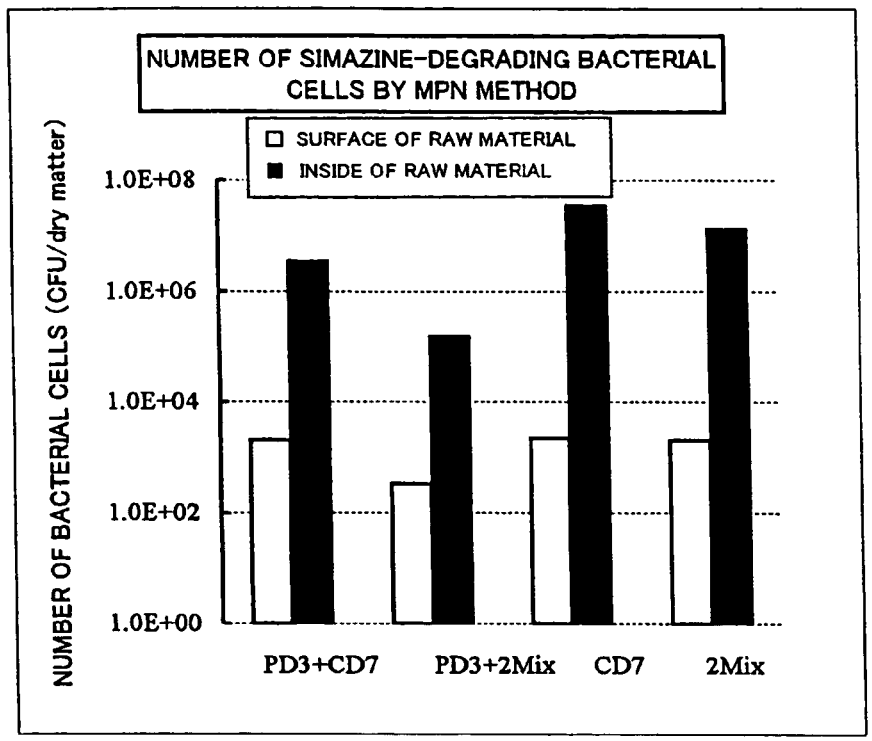
FIG. 7 is a graphical representation of the number of bacterial cells of the simazine-degrading bacteria enriched on the support for holding a complexed enrichment of degrading bacteria.

The number of bacterial cells of the PCNB-degrading bacteria on the surface of, or inside, a support for holding a complexed enrichment of degrading bacteria, on which various kinds of degrading bacteria were held, is shown in FIG. 6 and the number of bacterial cells of the simazine-degrading bacteria is shown in FIG. 7. From the above measurement, it is found that the levels of the number of degrading bacterial cells are in the range of $10^4$ to $10^7$ CFU/g dried product. In addition, for each degrading bacteria, it is found that the bacterial cells are enriched on the surface of the porous material (raw material surface) at a higher density than that inside the porous material (inside raw material).

4. Evaluation on Degradation Ability to Organic Contaminant [FIGS. 8 to 11]:

Assuming a method of decontaminating contaminated water by passing the contaminated water through a support for holding a complexed enrichment of degrading bacteria, the degradation ability of the support for holding a complexed enrichment of degrading bacteria for various kinds of organic contaminant was evaluated as follows. At first, a reflux device 1 shown in FIG. 2 was prepared. Then, the reflux device 1 was filled with 6.25 g of the support for holding a complexed enrichment of degrading bacteria (corresponding to 2.5 g of the dried product). Subsequently, 150 ml of an inorganic salt medium containing 5 ppm of simazine, 5 ppm of atrazine, 2.5 ppm of PCP, and 2.5 ppm of HCB was used as a reflux solution and then refluxed through the support for holding a complexed enrichment of degrading bacteria. The reflux solution was replaced with new one every one week. The reflux was carried out for three weeks in total. The degradation ability of the support for holding a complexed enrichment of degrading bacteria to various kinds of organic contaminant was evaluated by measuring the concentrations of various organic contaminants and the chlorine ion concentration in the reflux solution.

Figure 8:
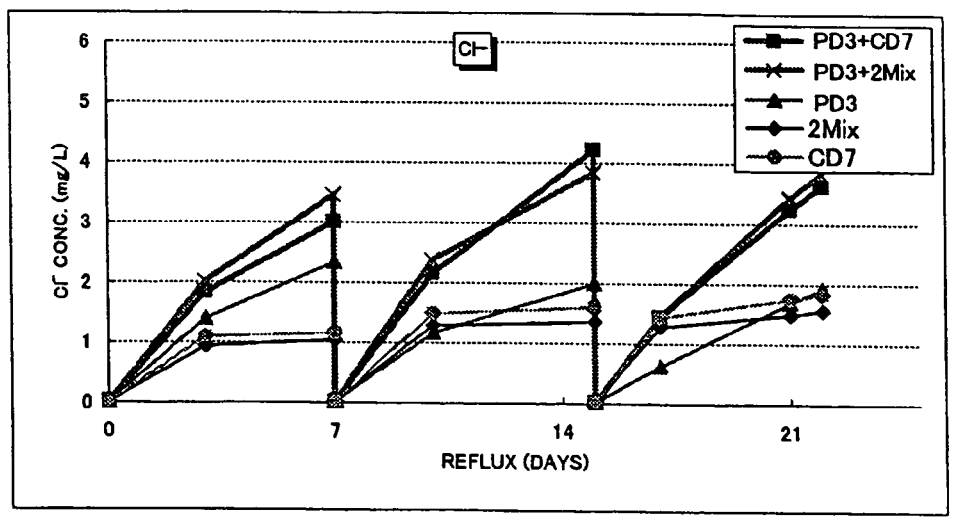
FIG. 8 is a graphical representation of the relationship between the number of reflux days and the concentration of chloride ion when an organic contaminant is refluxed through the support for holding a complexed enrichment of degrading bacteria.
Figure 9:
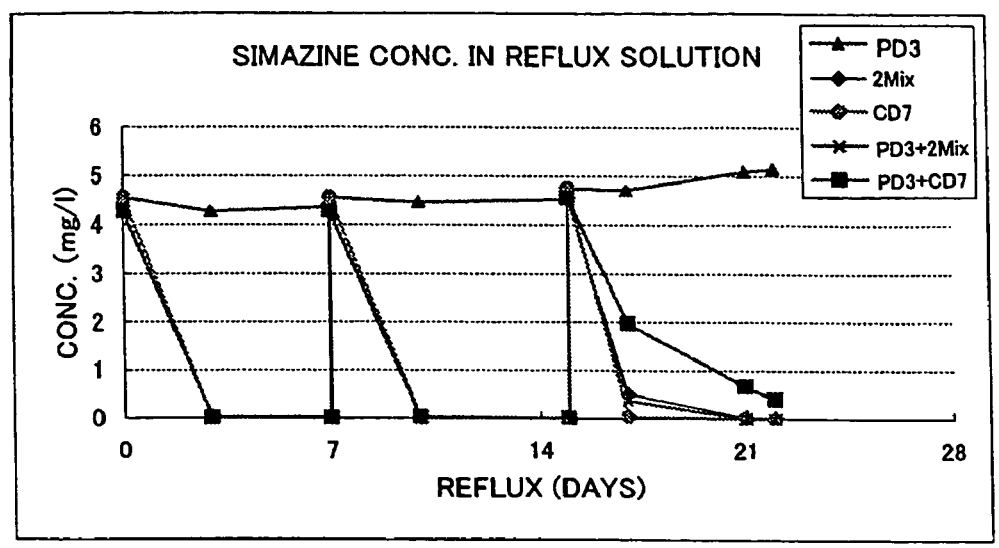
FIG. 9 is a graphical representation of the relationship between the number of reflux days and the concentration of simazine when an organic contaminant is refluxed through the support for holding a complexed enrichment of degrading bacteria.
Figure 10:
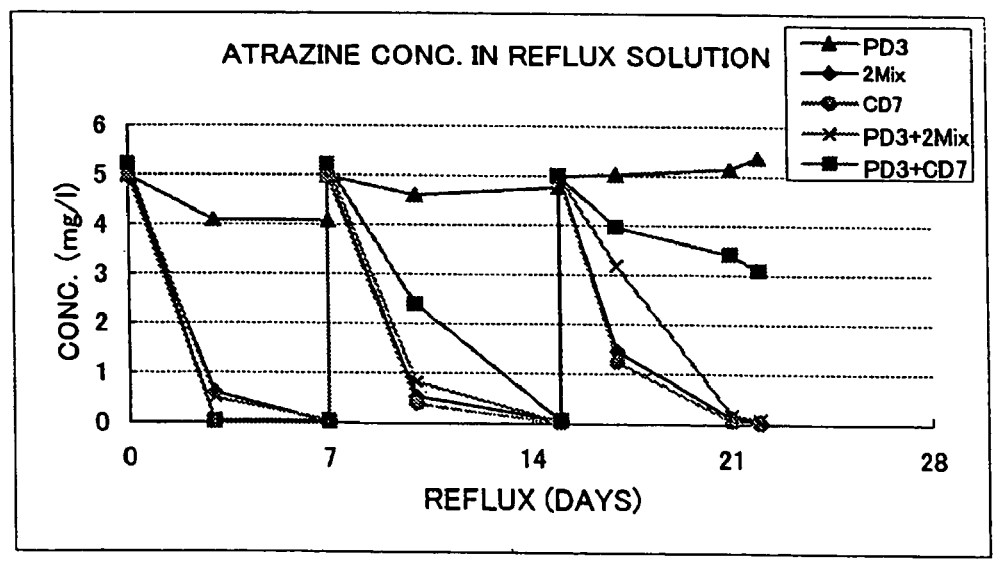
FIG. 10 is a graphical representation of the relationship between the number of reflux days and the concentration of atrazine when an organic contaminant is refluxed through the support for holding a complexed enrichment of degrading bacteria.
Figure 11:
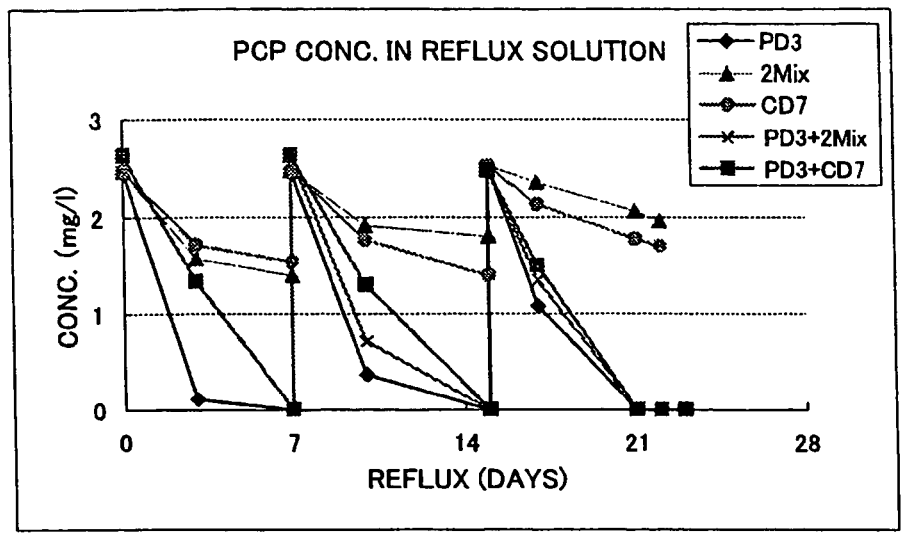
FIG. 11 is a graphical representation of the relationship between the number of reflux days and the concentration of PCP when an organic contaminant is refluxed through the support for holding a complexed enrichment of degrading bacteria.

The relationship between the number of reflux days and the chlorine ion concentration is shown in FIG. 8. In addition, the relationship between the number of reflux days and each of the simazine concentration, atrazine concentration, and PCP concentration is shown in each of FIGS. 9 to 11.

In the support for holding a complexed enrichment of degrading bacteria, which contained a complex system of PD3, CD7, and 2Mix, simazine, atrazine, and PCP were decomposed because of a decrease in concentration of each of organic contaminants. By the way, HCB was adsorbed on the sintered glass filter 2 used in the reflux device 1, so that the degradation ability cannot be evaluated sufficiently. In this case, however, it is found that the support may bear at least degradation ability.

From a decrease in concentration of each kind of organic contaminant, comparing with the single fraction, it is found that the number of degrading bacterial cells in the porous material can be decreased to about 1/100 to 1/10 in the case of the support for holding a complexed enrichment of degrading bacteria. However, from the results of decomposing various organic contaminants, the degradation ability to the organic contaminant is sufficient. In particular, the support for holding a complexed enrichment of degrading bacteria, on which PD3 and CFD7 are held (hereinafter referred to as "PD3/CD7-holding support" and the support for holding a complexed enrichment of degrading bacteria, on which PD3 and 2Mix are held (hereinafter, referred to as a PD3/2Mix-holding support) decompose PCNB and simazine 90% or more, respectively. In addition, atrazine and PCP, which are organic contaminants other than PCNB and simazine, can be decomposed 90% or more.

Furthermore, when the PD3/2Mix-holding support is compared with the PD3/CD7-holding support, from the difference between the amounts of chlorine ions generated, it is found that the PD3/CD7-holding support can enrich the degrading bacteria at a higher density than that of the PD3/2Mix-holding support.

Figure 12:
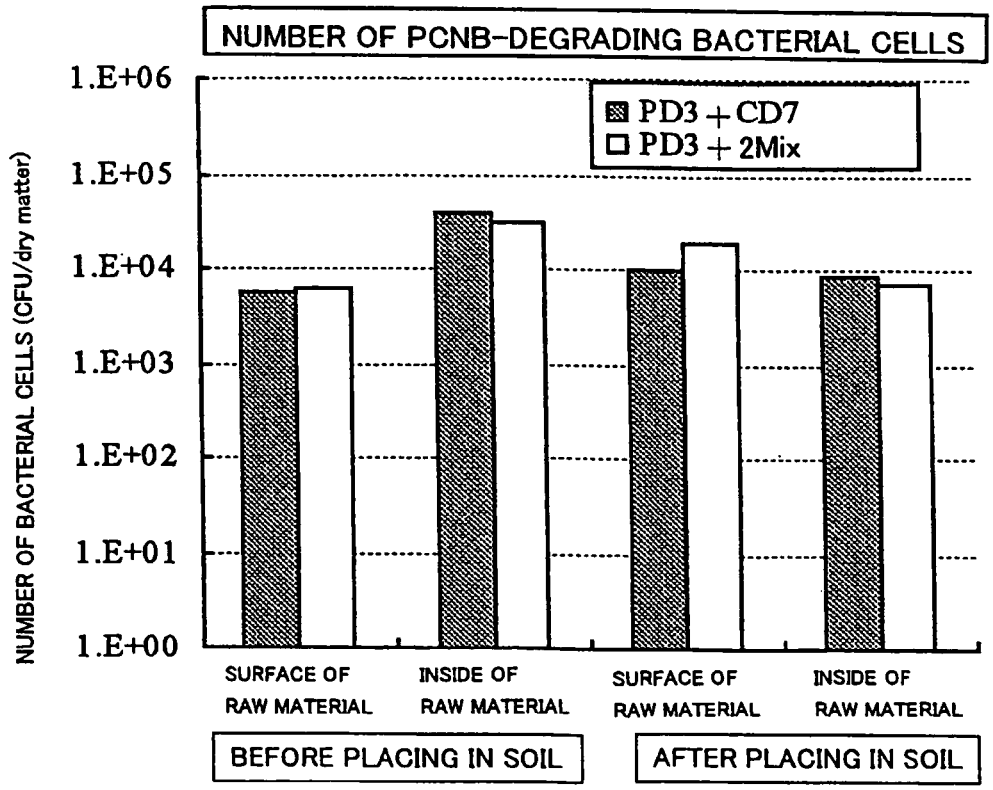
FIG. 12 is a graphical representation of the number of bacterial cells of the PCNB-degrading bacteria before and after a test of decomposing organic contaminants.
Figure 13:
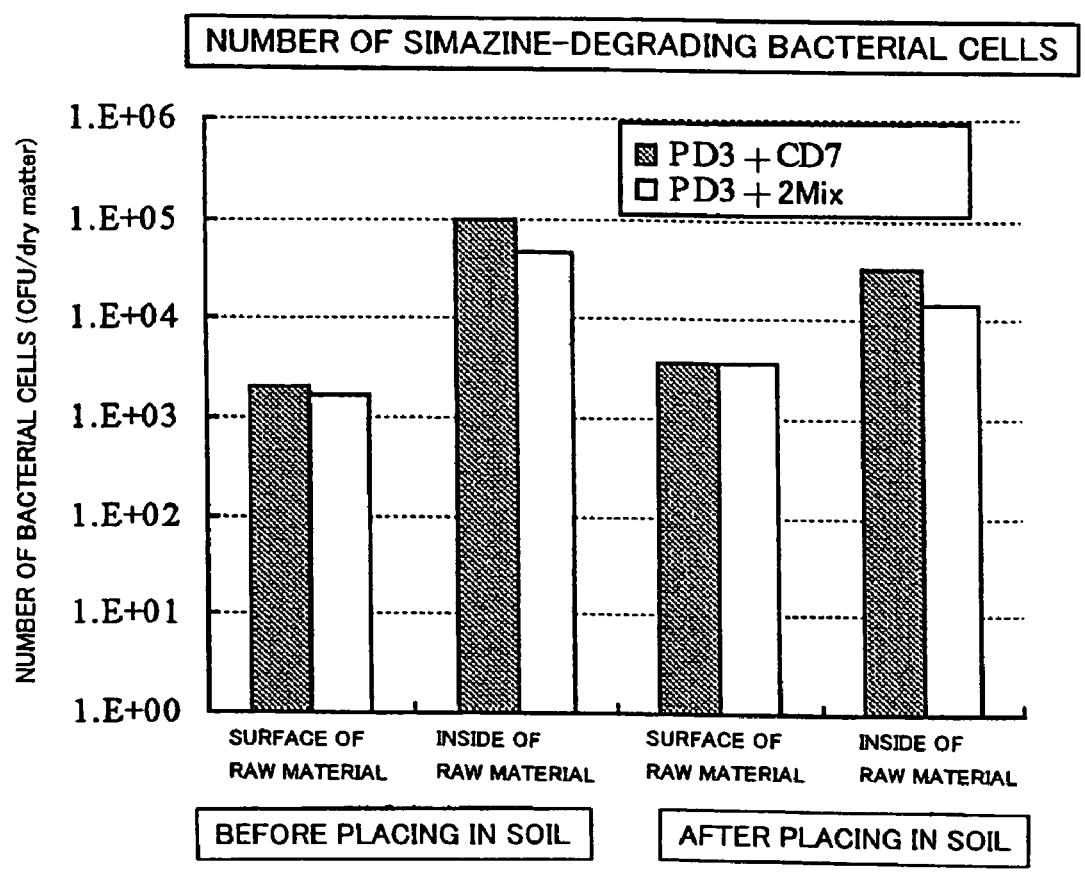
FIG. 13 is a graphical representation of the number of bacterial cells of the simazine-degrading bacteria before and after a test of decomposing organic contaminants.

5. Evaluation on the Degradation Ability to Organic Contaminant (2) [Table 1, FIGS. 12 and 13]

Assuming a method of decontaminating contaminated soil by mixing a support for holding a complexed enrichment of degrading bacteria in the soil, the degradation ability of the support for holding a complexed enrichment of degrading bacteria for various kinds of organic contaminant was evaluated separately from the above item (1) as follows. 80 g of plantation soil (soil texture: L, pH: 6.2, T-C: 0.9%, corresponding dried soil: 59.6 g) mixed with simazine (SI): 5 ppm, atrazine (AT): 5 ppm, PCP: 5 ppm, and HCB: 5 ppm was mixed with 15 g of a support for holding a complexed enrichment of degrading bacteria (corresponding to 6.0 g of dried product) and then filled into a column (5ϕ×7.5 cm). Subsequently, the column was allowed to stand for 4 weeks at 25° C. During such a period, the column was watered with 15 to 30 ml of water once per week and percolating water was then collected, followed by determining the concentration of each chemical. Furthermore, the concentration of each of the chemicals in the soil and the support for holding a complexed enrichment of degrading bacteria obtained after 4 weeks (after terminating the test) was measured, and the number of bacterial cells of each of the degrading bacteria on the surface of, and inside, the support for holding a complexed enrichment of degrading bacteria were determined by the MPN method in the same way as that of the method described above, respectively. The results are listed in Table 1 and shown in FIGS. 12 and 13.

TABLE 1

Remaining amounts and degradation rates of various chemicals in soil, carbonized ligneous material A, and percolating water after terminating the column test

| | Remaining amount | Control plot | | | | PD3 + CD7 | | | | PD3 + 2Mix | | | |
|---|---|---|---|---|---|---|---|---|---|---|---|---|---|
| | (mg) | SI | AT | PCP | HCB | SI | AT | PCP | HCB | SI | AT | PCP | HCB |
| Soil Material A | In dried soil | 0.078 | 0.098 | 0.075 | 0.149 | 0.058 | 0.064 | 0.059 | 0.135 | 0.061 | 0.065 | 0.062 | 0.138 |
| | In dried product | 0.198 | 0.181 | 0.205 | 0.135 | 0.002 | 0.002 | 0.002 | 0.003 | 0.002 | 0.003 | 0.002 | 0.003 |
| Percolating water | Remaining amount in total | 0.021 | 0.019 | 0.017 | 0.013 | 0.010 | 0.011 | 0.012 | 0.008 | 0.011 | 0.012 | 0.013 | 0.009 |
| | Whole remaining amount | 0.2974 | 0.2974 | 0.2967 | 0.2974 | 0.071 | 0.078 | 0.073 | 0.145 | 0.075 | 0.079 | 0.077 | 0.150 |
| | Degradation rate (%) | 0.2 | 0.2 | 0.4 | 0.2 | 76.2 | 73.9 | 75.5 | 51.2 | 74.9 | 73.5 | 74.1 | 49.6 |

Remark: Carbonized ligneous material A without enrichment of degrading bacteria was used as a control
Input amount of each chemicals into soil: 0.298 mg As is evident from Table 1, the support for holding a complexed enrichment of degrading bacteria (PD3 and CD7) and the support for holding a complexed enrichment of degrading bacteria (PD3 and 2Mix) showed extremely high degradation and removal abilities of about 75% in soil with respect to simazine, atrazine, and PCP but the abilities decreased to about 50% with respect to HCB. This is probably because the aqueous solubility of HCB is 0.005 ppm, which is extremely lower than those of the other chemicals, and thus the amount of HCB adsorbed in the porous material with the translocation/diffusion of water decreases by about 35% (see the control plot). In addition, from FIGS. 12 and 13, it is found that each of the PCNB-degrading bacteria PD3 and the simazine-degrading bacteria CD7 is enriched at a high density without a substantial change in the number of bacterial cells before and after placing in the soil. In addition, it is found that degrading bacterial cells are enriched at a higher density inside the porous material (inside raw material) than that on the surface of the porous material (the surface of the raw material). Furthermore, the total number of bacterial cells inside the porous material in which CD7 including CD7w is enriched is larger than that of the porous material in which 2Mix free of CD7w is enriched. It is found that CD7w may enhance the enrichment of bacterial cells inside the porous material.

Figure 14:
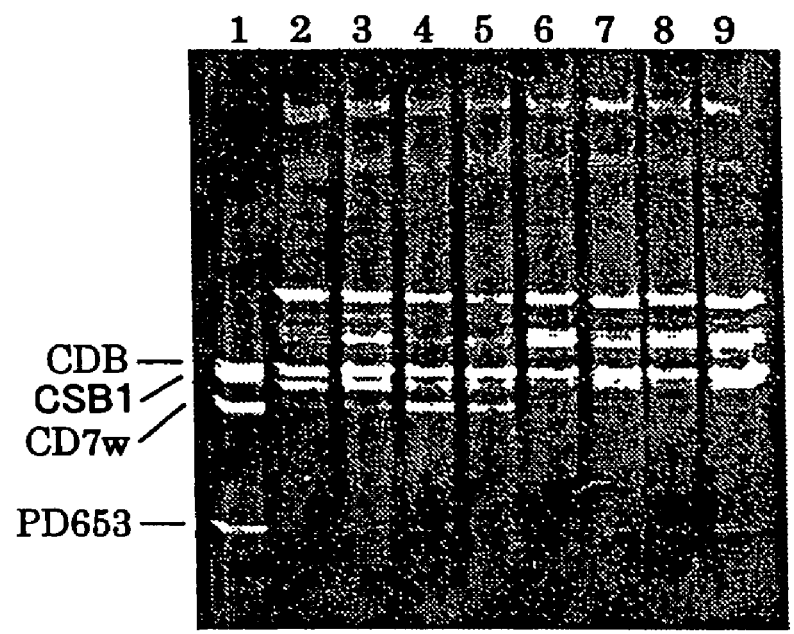
FIG. 14 is a diagram that represents the constituent bacteria in the support for holding a complexed enrichment of degrading bacteria by PCR-DGGE.

6. Enrichment of Degrading Bacteria in Porous Material [FIG. 14]:

Before and after mixing with soil, a $10^1$-fold dilute solution with a phosphate buffer was prepared from each of various supports for holding a complexed enrichment of degrading bacteria by the same method as one described above, and then bacterial cells and the porous material were collected by centrifugation. DNA in a sample of the surface of the porous material was extracted using FastDNA kit (Qbiogene, Co., Ltd.). DNA in a sample of the inside of the porous material (about 0.3 g) was extracted using FastDNA kit for SOIL (Obiogene, Co., Ltd.) after addition of 125 µl of SuperBlock (PIERCE, Co., Ltd.). The extracted DNA was subjected to PCR-DGGE with a Muyzer method to investigate and analyze the enrichment and transition of degrading bacteria to the porous material.

As shown in Table 14, the PCR-DGGE confirmed the enrichment of: PD653 constituting the PCNB-degrading bacteria PD3; and CDB21, CSB1, and CD7w constituting the simazine-degrading bacteria CD7 on the porous material. The amount of PD653 may be sufficient for the degradation of PCNB in spite of a small abundance ratio of PD653. It is found that almost no CD7w is present on the surface of the porous material but highly enriched inside the porous material. Therefore, the compatibility of the bacterial group to the porous material may be enhanced. There is no change in the configuration of a bacterial group enriched before and after mixing the support for holding a complexed enrichment of degrading bacteria in soil. In addition, neither adhesion nor inversion of a soil bacterial into the porous material was observed.

What is claimed is:

1. A biologically pure bacterial strain which is able to degrade PCNB, wherein the bacterial strain is *Nocardioides* sp. pD653, which has been deposited as FERM BP-10405.

* * * * *